United States Patent [19]

Steckel

[11] Patent Number: 4,925,983

[45] Date of Patent: May 15, 1990

[54] BORONATED COMPOUNDS

[75] Inventor: Thomas F. Steckel, Chagrin Falls, Ohio

[73] Assignee: The Lubrizol Corporation, Wickliffe, Ohio

[21] Appl. No.: 183,513

[22] Filed: Apr. 14, 1988

Related U.S. Application Data

[63] Continuation of Ser. No. 930,213, Nov. 12, 1986, abandoned.

[51] Int. Cl.$^5$ .............................................. C07F 5/02
[52] U.S. Cl. .......................................... 564/8; 44/64; 252/50
[58] Field of Search ............................................. 564/8

[56] References Cited

U.S. PATENT DOCUMENTS

| | | | |
|---|---|---|---|
| 3,000,916 | 9/1961 | Klass et al. | 260/404.5 |
| 3,087,936 | 4/1963 | Le Suer | 260/326.3 |
| 3,322,670 | 5/1967 | Burt et al. | 252/49.6 |
| 3,368,972 | 2/1968 | Otto | 252/47.5 |
| 3,649,229 | 3/1972 | Otto | 44/73 |
| 3,697,574 | 10/1972 | Piasek et al. | 564/8 |
| 3,703,536 | 11/1972 | Piasek et al. | 260/462 |
| 4,119,552 | 10/1978 | Davis et al. | 252/49.6 |
| 4,328,113 | 5/1982 | Horodysky et al. | 252/49.6 |
| 4,426,305 | 1/1984 | Malec | 252/49.6 |
| 4,454,059 | 6/1984 | Pindar et al. | 252/51.5 R |
| 4,533,481 | 8/1985 | Jahnke | 252/49.6 |
| 4,554,086 | 11/1985 | Karol et al. | 252/49.6 |

*Primary Examiner*—Anton H. Sutto
*Attorney, Agent, or Firm*—Forrest L. Collins; Frederick D. Hunter; Robert A. Franks

[57] ABSTRACT

This invention describes nitrogen containing compounds which are boronated in the presence of a protic material such as water or an alcohol or mixtures thereof.

19 Claims, No Drawings

BORONATED COMPOUNDS

This is a continuation of co-pending application Ser. No. 930,213, filed on Nov. 12, 1986, now abandoned.

BACKGROUND OF THE INVENTION

1. Field of the Invention

This invention deals with boronating organic compounds particularly those which are useful in lubricant compositions.

2. Description of the Art

Boron is a desirable ingredient for inclusion in lubricant compositions. The boron functions to protect metal surfaces apparently by forming a barrier between the metal surfaces which is effective to prevent scuffing and scraping. It is also extremely desirable in a lubricating composition or in the manufacture of an additive for a lubricating composition to have a product which incorporates the boron in a fully soluble or dispersible form within the lubricant. It is also desirable that the boron-containing compound or complex be clear to allow optical screening of the components for contaminants.

U.S. Pat. No. 4,328,113, issued May 4, 1982 to Horodysky et al, discloses that borated derivatives may be prepared by treating amines or diamines with boric acid in the presence of an alcoholic or hydrocarbon solvent. It is further stated that the presence of the solvent is not essential and it desired that the solvent be a non-reactive material such as isopropanol, a butanol or a pentanol.

Klass et al, in U.S. Pat. No. 3,000,916, issued Sept. 19, 1961, discloses that a tallow-derived propylene diamine may be reacted with a polymeric linoleic acid to form a hazy product. This product is then reacted with boric acid in methanol, followed by the addition of a hydrocarbon diluent oil, and thereafter having the entire reaction mixture stripped.

Malec, in U.S. Pat. No. 4,426,305, issued Jan. 17, 1984, teaches that the dispersancy of a lubricating oil is improved by the combination of (a) a boronated hydrocarbon-substituted succinic amide/imide/ester of an oxyalkylated amine and, (b) a Mannich condensation product of a hydrocarbon-substituted phenol, formaldehyde or amine, optionally including therein a fatty acid or boronating agent. Products having a boron content of 0.49%, are stated by Malec to be obtained from the reaction of a polyisobutenyl succinic anhydride with an oxyethylated polyethylene amine. The amine is said to be treated with boric acid and water in a 3:1 respective weight ratio. Malec teaches the resultant products as having a relatively low boron content and to give a clear, boronated succinimide dispersant.

Burt et al, in U.S. Pat. No. 3,322,670, issued May 30, 1967, describes the combination of an alkenyl substituted succinic anhydride, boric acid, boric acid anhydride or a boric acid ester, either as a solid or as a solution in a solvent such as dioxane, acetone or methanol or as a suspension in a light hydrocarbon oil. It is further stated by Burt that it is advantageous to employ as an aid for the combination a hydroxylic compound such as water or a lower ($C_1$ to $C_4$) alkanol such as methanol, ethanol, propanol, isopropanol, N-butanol, isobutanol and the like or mixtures of water with any one of the alcohols.

Piasek et al, in U.S. Pat. No. 3,703,536, issued Nov. 21, 1972, teaches that a boron to nitrogen weight ratio of 1.2:1 may be obtained in a di(alkenylsuccinimide) of $N_1,N_3$-symmetrical bis (aminopolyazalkylene) urea. The boronation is conducted by stirring a solution of the aforementioned component, heating it to 100° C., and adding in a slurry of boric acid in a 5W oil. Water is then added and the resulting stirred mixture heated to 138° C. and held at that temperature. Nitrogen gas is then injected into the hot liquid until all water and added water (about 1.5 moles of water per mole of the boric acid employed) is driven off. The boron content of the product is stated to be 2.5%.

LeSuer, in U.S. Pat. No. 3,087,936, issued Apr. 30, 1963, teaches that the reaction of acylated nitrogen compositions with boron compounds can be effected by simply mixing the reactants at the desired temperature. An inert solvent is optionally included in the LeSuer reaction, especially when a highly viscous or solid reactant is present in the reaction mixture. The inert solvents of LeSuer may be a hydrocarbon such as benzene, toluene, naphtha, cyclohexane, n-hexane or mineral oil. It is further taught by LeSuer that water may be removed from the reaction mixture as it is formed.

Davis et al, in U.S. Pat. No. 4,119,552, issued Oct. 10, 1978, teaches that organic materials may be boronated and that any excess boronating agent may be removed by standard means such as filtration, or by washing with water, alcohols or mixtures thereof. It is further suggested when a solid is employed in the boronation reaction that hydrocarbons such as hexane, octane, nonane, toluene, xylene, mineral oil and the like be employed. Davis et al also allow for the use of chlorinated hydrocarbons as solvents including chlorobenzene, dichlorobenzene and the like.

U.S. Pat. No. 4,533,481, issued Aug. 6, 1985 to Jahnke discloses that inhibitors which comprise mixtures of monoamine salts of polycarboxylic acids and boric acid may be used to prevent the corrosion of metal surfaces contacting aqueous systems. Jahnke contemplates the use of mixtures comprising 15-30% by weight of a polycarboxylic acid, 5-20% by weight of a boron acid, 40-55% by weight of a monoamine and the remainder is water. It is further stated that generally from 10-30% by weight of the mixture is water.

U.S. Pat. No. 4,554,086 to Karol et al, issued Nov. 19, 1985, teaches that lubricating oils of an improved wear resistance and dispersancy are obtained containing borate esters of hydrocarbyl-substituted mono- and bis-succinimides containing polyamine chain linked hydroxyacyl groups. Karol teaches that the boric acid is added to his reaction mixture (to be boronated) as a 5-50% weight slurry in a diluent oil. Karol further states that the water of reaction is removed as it is formed.

It is, therefore, desirable to find a manner to effectively incorporate boron into a compound containing an amine group or a salt thereof wherein the compound also contains an amide, imide or Mannich based structure. It is desirable to chemically incorporate as much boron as possible to obtain a clear solution and a high degree of stable boron in the product. The boron is desirably a part of the amine compound and not present as a inorganic polyborate salt. It is further desirable to obtain a fast and efficient method of incorporating the boron into the reaction product without removing the water of reaction as it is formed.

The present invention deals with the foregoing goals as hereinafter described. Throughout the specification and claims, ratios and percentages are by weight, temperatures are in degrees Celsius and pressures are in Kpa gauge, unless otherwise indicated. References to patents and literature articles cited herein are incorporated by reference.

SUMMARY OF THE INVENTION

This invention describes a process for boronating an amide, imide or Mannich base containing compound including the steps of mixing:

(a) a compound containing an amide, imide or Mannich base group which has present at least one amine group or salt thereof;

(b) a boronating agent, and;

(c) a protic compound in a weight ratio to the boronating agent of at least about 1:2, and;

(d) obtaining the boronated compound.

A further embodiment described herein is a process for boronating a compound containing an amine group including the steps of mixing:

(a) a compound containing at least one amine group;

(b) a boronating agent, (c) water, and (d) an alcohol wherein the combined weight of the water and the alcohol present is at least about 1 part per parts of the boronating agent, and (e) obtaining the boronated compound. The compounds of each of the above processes, as well as their uses in lubricants, greases and fuels is described herein.

DETAILED DESCRIPTION OF THE INVENTION

The present invention as previously noted deals with obtaining boronated organic compounds having a high degree of boron content and which are preferably substantially clear upon manufacture (e.g., prior to a filtration operation). The problem, generally, in boronating organic compounds is that the boron may form polymers which are not chemically a part of the organic product but which are sufficiently soluble in the organic phase to cause a haze. While such products may be filtered to produce a clear product, the filtration removes the polymeric boron, thus, diminishing the boron content of the product. The boron, when in a polymeric form, is not particularly useful in the lubricant products as compared to a chemically combined boron in the organic material.

This invention details the manner in which boron may be incorporated into the product at a high level to give a product which is substantially clear without filtration.

The first component to be discussed in the present invention is the organic compound which is to be boronated. The organic compounds suggested for boronation herein are those organic compounds containing at least one amine group or a salt thereof which also contains at least one structure which is an amide, imide or Mannich base. The compound to be boronated must be capable of reacting with boron. That is, the organic compound and the boron must be capable of forming a chemical bond.

A preferred source of the amide and imide containing compounds which may be employed herein and which contain an amine group or which may be converted to a salt thereof are obtained from acylated nitrogen compositions. The acylated nitrogen compositions are typically prepared such that they contain a relatively polar group and a relatively oleophilic group. The oleophilic group contains a substantially hydrocarbon substituent and is described as follows.

The substantially hydrocarbon substituent of the acylated nitrogen compositions preferably should be substantially free from large oil-solubilizing pendant groups, i.e., groups having more than about 6 aliphatic carbon atoms. While some large oil-solubilizing pendant groups may be present, they preferably should be present in proportions less than about one such group for every 25 aliphatic carbon atoms in the main hydrocarbon chain. A higher proportion of large pendant groups impairs the effectiveness of the acylated nitrogen compositions as additives in hydrocarbon oils.

The substantially hydrocarbon substituent may contain polar substituents provided, however, that the polar substituents are not present in proportions sufficiently large to alter significantly the hydrocarbon character of the radical. The polar substituents are exemplified by chloro, bromo, keto, ethereal, aldehydo, and nitro, etc. The upper limit with respect to the proportion of such polar substituents in the radical is approximately 10% based on the weight of the hydrocarbon portion of the radical.

The sources of the substantially hydrocarbon substituent include principally the high molecular weight substantially saturated petroleum fractions and substantially saturated olefin polymers, particularly polymers of mono-olefins having from 2 to about 30 carbon atoms. The especially useful polymers are the polymers of 1-mono-olefins such as ethylene, propene, 1-butene, isobutene, 1-hexene, 1-octene, 2-methyl-1-heptene, 3-cyclohexyl-1-butene and 2-methyl-5-propyl-1-hexene. Polymers of medial olefins, i.e., olefins in which the olefinic linkage is not at the terminal position, likewise are useful. They are illustrated by 2-butene, 3-pentene, and 4-octene.

Also useful are the interpolymers of the olefins such as those illustrated above with other interpolymerizable olefinic substances such as aromatic olefins, cyclic olefins, and polyolefins. Such interpolymers include, for example, those prepared by polymerizing isobutene with styrene; isobutene with butadiene; propene with isoprene; ethylene with piperylene; isobutene with chloroprene; isobutene with p-methyl styrene; 1-hexene with 1,3-hexadiene; 1-octene with 1-hexene; 1-heptene with 1-pentene, 3-methyl-1-butene with 1-octene; 3-3-dimethyl-1-pentene with 1-hexene; isobutene with styrene and piperylene; etc.

The relative proportions of the mono-olefins to the other monomers in the interpolymers influence the stability and oil-solubility of the final acylated nitrogen compositions derived from such interpolymers. Thus, for reasons of oil-solubility and stability the interpolymers contemplated for use in this invention should be substantially aliphatic and substantially saturated, i.e., they should contain at least about 80%, preferably at least about 95% on a weight basis of units derived from the aliphatic mono-olefins and no more than about 5% of olefinic linkages based on the total number of carbon-to-carbon covalent linkages. In most instances, the percentage of olefinic linkages should be less than about 2% of the total number of carbon-to-carbon covalent linkages.

Specific examples of such interpolymers include the copolymer of 95% (by weight) of isobutene with 5% of styrene, terpolymer of 98% of isobutene with 1% of piperylene and 1% of chloroprene; terpolymer of 95% of isobutene with 2% of 1-butene and 3% of 1-hexene; terpolymer of 60% of isobutene with 20% of 1-pentene and 20% of 1-octene; copolymer of 80% of 1-hexene and 20% of 1-heptene; terpolymer of 90% of isobutene with 2% of cyclohexene and 8% of propene; and copolymer of 80% of ethylene and 20% of propene.

Another source of the substantially hydrocarbon radical comprises saturated aliphatic hydrocarbons such as highly refined high molecular weight white oils or synthetic alkanes such as are obtained by hydrogenation of high molecular weight olefin polymers illustrated above or high molecular weight olefinic substances.

The use of olefin polymers having molecular weight of about 750–5000 is preferred. Higher molecular weight olefin polymers having molecular weights from about 10,000 to about 100,000 or higher have been found to impart also viscosity index improving properties to the acylated nitrogen compositions of this invention. In many instances the use of such higher molecular weight olefin polymers is desirable.

The overall molecular weight of component (A) may vary considerably including compounds having a molecular weight of preferably at least 250, more preferably greater than 750, most preferably greater than 900. Component (A) preferably varies between a molecular weight of 750 (or 900) to 30,000.

The relatively polar group of the acylated nitrogen compositions is selected from the class consisting of acyl, acylimidoyl and acyloxy radicals. These radicals have the following structural configurations, respectively:

$R_1C(O)-$, $R_1C(=NR_2)-$, and $R_1CO_2-$ wherein $R_1$ represents the substantially hydrocarbon substituent described hereinbefore and $R_2$ represents a hydrogen radical or an organic radical such as a hydrocarbon radical or a polar-substituted hydrocarbon radical.

Component (A) contains at least one basic nitrogen group. Such groups include:

$RNH_2$, $(R)_2NH$ or $N(R)_3$ where R is an organic moiety, e.g., primary, secondary or tertiary amine groups. The compounds from which the nitrogen-containing group may be derived include principally aliphatic amines, aromatic amines, heterocyclic amines or carbocyclic amines. The amines are preferably primary or secondary amines and may also be polyamines such as alkylene amines, arylene amines, cyclic polyamines and the hydroxy-containing derivatives of such amines.

Specific amines of these types are methylamine, N-methyl-ethylamine, N-methyl-octylamine, N-cyclohexylaniline, dibutylamine, cyclohexylamine, aniline, di(p-methylphenyl)amine, dodecylamine, octadecylamine, o-phenylenediamine, N,N'-di-n-butyl-p-phenylene-diamine, morpholine, piperazine, tetrahydropyrazine, indole, hexahydro-1,3,5-triazine, melamine, bis-(p-aminophenyl) methane, phenyl-methylenimine, menthanediamine, cyclohexamine, pyrrolidine, 3-amino 5,6-diphenyl-1,2,4-triazine, quinonediimine, 1,3-indandimine, 2-octadecylimidazoline, 2-phenyl-4-methyl-imidazolidine, oxazolidine, ethanolamine, diethanolamine, and 2-heptyloxazolidine.

A preferred source of the nitrogen-containing group consists of polyamines, especially alkylene amines conforming for the most part to the formula HN(A)[alkylene N(A)]$_n$H wherein n is an integer preferably less than about 50, A is a substantially hydrocarbon or hydrogen radical, and the alkylene radical is preferably a lower alkylene radical having less than about 8 carbon atoms. The alkylene amines include principally methylene amines, ethylene amines, butylene amines, propylene amines, pentylene amines, hexylene amines, heptylene amines, octylene amines, other polyamines, and also the cyclic and the higher homologs of such amines such as piperazines and amino-alkyl-substituted piperazines. They are exemplified specifically by: ethylene diamine, triethylene tetramine, propylene diamine, decamethylene diamine, octamethylene diamine, di(heptamethylene) triamine, tripropylene tetramine, tetraethylene pentamine, trimethylene diamine, pentaethylene hexamine, di(trimethylene)triamine, 2-heptyl 3-(2-aminoethyl) imidazoline, 4-methyl-imidazoline, 1,3-bis-(2-aminoethyl) imidazoline, pyrimidine, 1-(2-amino propyl)piperazine, 1-4-bis(2-aminoethyl) piperazine, and 2-methyl-1-(2-aminobutyl)piperazine. Higher homologs such as are obtained by condensing two or more of the above illustrated alkylene amines likewise are useful.

The ethylene amines are especially useful. They are described in some detail under the heading "Ethylene Amines" in "Encyclopedia of Chemical Technology." Kirk and Othmer, volume 5, pages 898–905, Interscience Publishers, New York (1950). Such compounds are prepared most conveniently by the reaction of an alkylene chloride with ammonia. The reaction results in the production of somewhat complex mixtures of alkylene polyamines. These mixtures find use in the process of this invention. On the other hand, quite satisfactory products may be obtained also by the use of pure alkylene amines. An especially useful alkylene amine for reasons of economy as well as effectiveness of the products derived therefrom is a mixture of ethylene amines prepared by the reaction of ethylene chloride and ammonia and having a composition which corresponds to that of tetraethylene pentamine.

Hydroxyalkyl-substituted alkylene amines, i.e., alkylene amines having one or more hydroxyalkyl substituents on the nitrogen atoms, likewise are contemplated for use herein. The hydroxyalkyl-substituted alkylene amines are preferably those in which the alkyl group is a lower alkyl group, i.e., having less than about 6 carbon atoms. Examples of such amines include N-(2-hydroxyethyl)ethylene, diamine, 1-(2-hydroxyethyl) piperazine, mono-hydroxypropyl-substituted diethylene triamine. 1,4-bis(-hydroxypropyl)piperazine, dihydroxypropyl-substituted tetraethylene pentamine, N-(3-hydroxypropyl) tetramethylene diamine and 2-heptadecyl-1-(2-hydroxyethyl) imidazoline.

Higher homologs such as are obtained by condensation of the above-illustrated alkylene amines or hydroxy alkyl-substituted alkylene amines through amino radicals results in a higher amine accompanied with removal of ammonia and that condensation through the hydroxy radicals results in products containing ether linkages accompanied with removal of water.

Other sources of the nitrogen-containing group include ureas, thioureas, hydrazines, guanidines, amidines, amides, thioamides, cyanamides, etc. Specific examples illustrating such compounds are: hydrazine, phenylhydrazine, N,N'-diphenylhydrazine, octadecylhydrazine, benzoylhydrazine, urea, thiourea, N-butylurea, stearylamide, oleylamide, guanidine, 1,3- diphenylguanidine, 1,2,3-tributylguanidine, benzamidine, octadecamidine, N,N'-dimethylstearamidine, cyanamide, dicyandiamide, guanylurea, aminoguandine, etc.

As indicated previously, the nitrogen-containing group in the acylated nitrogen compositions are preferably characterized by a nitrogen atom attached directly to the relatively polar group. Thus, the acylated nitrogen compositions of this invention are characterized by amide, imide, amidine, or salt linkages and in many instances a mixture of such linkages. Those containing two such linkages separated by a lower alkylene radical (i.e., one having less than about 6 carbon atoms), such as are derived from succinic, glutaric, or adipic radicals, are especially preferred in this invention.

A convenient method for preparing the acylated nitrogen compositions comprises reacting a high molecular weight acid-producing compound characterized by the presence within its structure of a high molecular weight oil-solubilizing group having at least about 50 aliphatic carbon atoms and at least one acid-producing group having the structural configuration:

—C(O)X wherein X is selected from the class consisting of halogen, hydroxy, hydrocarbon-oxy, and acyloxy radicals, with at least about one-half an equivalent amount of a nitrogen-containing compound characterized by the presence with its structure of at least one radical having the structural configuration:

N—H

The above process involves a reaction between the acid-producing group with the nitrogen-containing radical to result in the direct attachment of the nitrogen atoms to a polar radical, i.e., acyl, acylimidoyl, or acyloxy radical derived from the acid-producing group. The linkage formed between the nitrogen atom and the polar radical may, thus, be that representative of a salt, amide, imide, or amidine radical. In most instances, the product of the above process contains a mixture of linkages representative of such radicals. The precise relative proportions of such radicals in the product usually are not known as they depend to a large measure upon the type of the acid-producing group and the nitrogen-containing radical involved in the reaction and also upon the environment (e.g., temperature) in which the reaction is carried out. To illustrate, the reaction involving an acid or anhydride group with an amino nitrogen-containing radical at relatively low temperatures such as below about 60° C. results predominantly in a salt linkage
(i.e., —C(O)O<sup>−</sup>H<sup>+</sup>N(R)<sub>3</sub>) 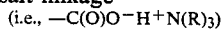

where R is H or an organic moiety, but at relative high temperatures such as above about 80° C. results predominantly in an amide, imide, or amidine linkage
(i.e., —C(O)(R)<sub>2</sub> or —C(=N—)N(R)<sub>2</sub> 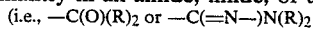

In any event, however, the products obtained by the above process, irrespective of the nature or relative proportions of the linkages present therein, have been found to be effective as additives in hydrocarbon oils for the purposes of this invention.

The Mannich derivatives, which are useful in the present invention, may be obtained as described in U.S. Pat. Nos. 3,368,972 and 3,649,229, both of which were issued to Otto, on Feb. 13, 1968 and Mar. 14, 1972, respectively. Further disclosures of the process for making Mannich compounds useful in the present invention are found in Pindar et al, U.S. Pat. No. 4,454,059, issued June 12, 1984. Simply stated, the Mannich materials may be obtained herein by reacting a polyaromatic compound of the formula Ar(OH)$_x$, where x is 1 or 2 with an aldehyde, preferably a lower aliphatic aldehyde. Suitable aldehydes include formaldehyde, benzaldehyde, acetaldehyde, the butyraldehydes, hydroxybutyraaldehydes and heptanals. Also suitable are aldehyde precursors such as paraformaldehyde, paraaldehyde, formalin, and methal. Formaldehyde and its polymers (e.g., paraformaldehyde and trioxane) are preferred. If desired, and such may well be desired to obtain sufficient hydrocarbon solubility or dispersibility of the Mannich base, then a hydrophobic tail may be added to the aromatic moiety utilized to form the Mannich compound. The number of hydrocarbon substituents on the aromatic moiety are preferably at least 1 and more preferably not more than 2 aliphatic or alicyclic substituents. It is also desired that the substituent have an average of at least 6, preferably at least 30 carbon atoms. Such substituents are typically derived from the polymerization of olefins such as ethylene, propylene, 1-butene, 2-butene, isobutene and the like. The Mannich bases described herein provide the amine required in component (a).

The next aspect of the invention to be discussed is the boronating agent. The boronating agent is conveniently any boron-containing compound which will react chemically with the organic compound previously described. The boronating agent may be boron trioxide or any of the various forms of boric acid including metaboric acid, orthoboric acid and tetraboric acid. A boric acid, and especially orthoboric acid is preferred herein.

The protic compounds which are useful herein to obtain the chemically bonded boron within the boronated organic compound includes such materials as water, alcohols, phenols, alkylated phenols, mercaptans and amines, particularly ethanolamine or ammonia. The preferred protic solvent is water or a lower alcohol and especially mixtures of the two. The protic alcohols especially useful include methanol, ethanol, propanol, isopropanol, n-butanol, 2-butanol and mixtures thereof. Conveniently, the lower alcohol may contain up to about 10 carbon atoms. Monohydric alcohols are preferred when the protic compound is an alcohol.

Where mixtures of water and a lower alcohol are utilized, it is preferred that the weight ratio of the water to the alcohol be from about 10:1 to about 1:5, preferably from about 5:1, to about 1:3.

The nitrogen to the boron equivalent ratio in component (a) to component (b) is conveniently from about 4:1 to about 1:2; preferably from about 2:1 to about 1:1. The weight ratio of the water added to the reaction mixture, is preferably utilized in at least a 1:2 preferably at least a 3:5, and more preferably at least a 4:5 weight ratio to the boronating agent. The alcohol, when utilized as the protic solvent herein, is conveniently employed to the boronating agent at a weight ratio of from about 10:1 to about 1:2. If methanol is used as the protic solvent, the weight ratio should be at least 2.5:1 to the boronating agent. The combined weight of the alcohol and water to the boronating agent is conveniently at least a 1:2 ratio, preferably at least 1:4 and is often used in a 1:1 to a 2:1 weight ratio.

The reaction of the present invention is conveniently conducted in an inert solvent such as mineral oil, toluene, or any other suitable oil soluble solvent. The temperature for reacting the boronating compound and the amine compound is conveniently between 50° C. and 180° C., preferably 65° C. and 160° C. The boron content of the products of the reaction are conveniently between 0.25% and 7% by weight, preferably between 0.5% and 5% by weight. The boronation should be conducted such that the protic compound is present with component (a) during substantially the entire time that boronation occurs to a substantial degree.

The products described herein are useful in lubricants, greases and fuels to provide a dispersant with added wear properties due to the boron incorporation. The amount of the reaction product employed in a grease, lubricant or fuel is conveniently in a minor proportion to a major portion of the grease, lubricant or fuel. The lubricants are natural or synthetic oils, while the fuels are usually liquid hydrocarbons such as gasoline or diesel fuel. The products are typically suggested for use in a lubricant, grease or fuel at about 0.05% to 5% by weight.

COMPARATIVE EXAMPLE

A boronated product is prepared by charging a 1 liter flask equipped with a stirrer, thermowell, and Dean Stark trap with a polyisobutenyl substituted succinimide. The polyisobutenyl substituents on the succinimide have an approximate molecular weight of 900. The imide portion of the molecule is obtained from amine still bottoms from the production of ethylene-diamine, triethylenetetramine, and tetraethylenepentamine. The overall molecular weight of the succinimide is approximately 2000–4000. The succinimide is maintained at approximately 70° C. to facilitate stirring of the reaction mixture.

Boric acid ($H_3BO_3$) is added to the succinimide in the reaction flask at a temperature between 66° C.–70° C. over a period of approximately 3 minutes. At this time, a nitrogen blanket at 0.15cfh (4.2 1/hour) is started. The reactants are maintained under the nitrogen blanket at 160° C. for ¾ of an hour. The reaction mixture is hazy and some solid material is observed at the top portions of the reaction vessel.

Between 16 and 18 grams of aqueous material is obtained in the trap as the water of reaction. The reaction mixture has a JTU* (Jackson Turbidity Units) rating of greater than 500. The percent volume of solids before filtration is 9%, most of which is believed to be inorganic boron polymers. Following filtration, a rating of 39 JTU's is obtained on this product. The found value for boron incorporation is 1.63% out of a theoretical 1.82%. The percent nitrogen incorporation is 2.21% out of a theoretical value of 2.36%.

This Example shows with the JTU value of greater than 500 that some boron may be physically mixed into the product but is not chemically incorporated, results in a hazy product and which upon filtration will result in a substantial loss of boron to the composition.

\* - a measure of the clarity of the product.

EXAMPLE I

A polyisobutylene substituted succinimide is obtained wherein the polyisobutylene units have a molecular weight of approximately 900 and the equivalent weight of the succinimide is 550. The amine utilized to prepare the succinimide is from polyethylene polyamine production, e.g., ethylenediamine, diethylenetriamine, triethylenetetraamine, and tetraethylenepentamine. The boronating agent utilized in this Example is boric acid ($H_3BO_3$) The reaction herein is conducted in a 1 liter flask equipped with a stirrer, thermowell, a below the liquid surface nitrogen inlet and a Dean-Stark trap. The succinimide is charged to the flask and the boric acid is added over a period of about six minutes at 70° C. to 78° C. The succinimide and the boric acid are present at a level of 1 equivalent of boron per equivalent of nitrogen in the succinimide. To the one equivalent of succinimide and one equivalent of boric acid is added 3.3 moles of water. The temperature is gradually increased to 162° C. over a period of approximately two to four hours. A nitrogen blanket results in cooling the reaction mixture to 150° C. over the course of one hour with the nitrogen flow rate set at 4.2 liters per hour.

The water, including that of the water of reaction, is removed through the use of the trap.

The resultant product has a JTU rating of 132 and before filtration 0.05% solids is obtained. The filtered product has a JTU score of 66 and has resulted in a boron content of 1.88% out of a theoretical 1.82% being incorporated. While the theoretical incorporation is greater than 100%, this is within acceptable error and shows that a high degree of boron incorporation has occurred in the product. The percent nitrogen incorporation is 2.32% out of a possible 2.36%. The foregoing Example shows the value of adding water in about a 1:1 weight ratio to the boronating agent.

EXAMPLE II

A succinimide dispersant according to Example I is charged to a glass walled reaction vessel equipped for heating and stirring. Boric acid (0.9 equivalents) is charged to the reaction vessel containing 0.9 equivalents of nitrogen (as the succinimide). To the reaction mixture is added 0.67 moles of n-butanol such that the weight ratio of the boric acid to the butanol is 1:0.9. The reaction mixture prior to the addition of the butanol is at 70° C. to 75° C. and the temperature following the addition of the butanol is raised to 103° C. The product is stripped at 160° C. to remove the water of reaction and the butanol.

The unfiltered product has a JTU rating of 400 while the filtered product has a JTU rating of 49. The percent boron incorporated in the product is 100% theoretical amount while the nitrogen found by analysis is 2.27% out of a theoretical 2.36%.

An observation of the product of the reaction indicates that substantially all of the boron has been chemically incorporated into the organic nitrogen compound.

EXAMPLE III

A succinimide dispersant, according to Example I is obtained and combined with boric acid. The nitrogen in the dispersant to the boron is at a 1:1 equivalent ratio. A premixed sample of water and n-butanol in a ratio of the boric acid to the water of 1:0.9 and a boric acid to butanol ratio of 1:0.45.

The boric acid, water and butanol are added between 78° C. and 84° C. and the temperature is slowly increased to 110° C. over a period of several hours. The water and butanol are stripped by heating to 150° C.

The product appears clear after stripping and has an unfiltered JTU rating of 43 and 0.04% of solids. The JTU rating after filtration is 24.

This Example shows the value of using an alcohol and water in combination with one another to obtain a product which is clear without filtration and of even greater clarity upon following filtration. The 0.04% solids before filtration indicates that substantially all of the boron is chemically combined in the organic molecule.

EXAMPLE IV

A succinimide dispersant is obtained as in Example I. The succinimide dispersant is placed in a suitable reaction vessel containing a stirring mechanism and heated to approximately 85° C. Boric acid is utilized to boronate the succimide compound wherein the ratio of nitrogen equivalents from the succinimide to the boron from the boric acid is 1:1.25. The weight ratio of boric acid to water utilized in this Example is 1:0.9 and the alcohol employed is n-butanol wherein the boric acid to butanol weight ratio is 1:0.5.

The water, boric acid and butanol are rapidly added to the reaction mixture at 85° C. and maintained at approximately 92° C. and held for a sufficient amount of time to substantially incorporate the boron into the organic product.

The water (including the water of reaction) and butanol are removed between 110° C. and 155° C.

By analysis, 2.3% of the product obtained is boron out of a theoretical 2.23%. The level of nitrogen incorporation of the product is 2.29% out of a theoretical 2.32%. The JTU rating of the unfiltered material is 136 and 120 after.

EXAMPLE V

A succinimide dispersant is obtained as in Example I with the exception that the polyisobutylene portion of the succinimide molecule has a molecular weight of approximately 2,000. The succinimide is charged to a suitable reaction vessel and heated to approximately 85° C. Boric acid is utilized to boronate the succinimide compound. The nitrogen from the succinimide to the boron equivalent ratio is 1:1. A mixture of water and butanol are utilized to facilitate the boronation in this Example.

The weight ratio of boric acid to the added water is 1:1.3. The boric acid to butanol ratio is 1:0.65.

The boric acid, water and butanol are added at approximately 85° C. and the temperature is gradually raised to 92° C. The product is stripped over a period of approximately five hours by heating to 160° C.

The JTU rating is 34 while the filtered JTU score is 26 for the foregoing product. The product is found to contain the theoretical 100% boron incorporation (0.42%). The nitrogen content of the product is found to be 1.11% while the theoretical nitrogen content is 1.08%. The succinimide dispersant has nitrogen equivalent weight of 1273 in this Example.

EXAMPLE VI

The succinimide dispersant of the preceding Example is heated to a temperature of 85° C. The boronating agent utilized in this Example is boric acid. The nitrogen in the dispersant to the boron equivalent ratio is 1:1. The boric acid to water equivalent ratio employed herein is 1:1.3. The alcohol employed herein is n-butanol and is employed at a weight ratio of 0.65:1 to the boric acid.

The water, boric acid and butanol are added at between 80° C. and 83° C., heated to 92° C. and held until the reaction is substantially complete. The product is first stripped at 143° C and held at 160° C until substantially all of the water and butanol are removed.

The product is substantially clear prior to filtration and has an unfiltered JTU score of 47. Following filtration, the JTU score is 29.

The amount of boron incorporated in the product is 0.64% out of a theoretical 0.76%. The theoretical amount of nitrogen in the product is 0.99% and 1% is found.

The foregoing example may be modified by using metaboric acid with substantially similar results. The process may also be modified by utilizing glycerine in place of the butanol. A similar product is obtained when isopropanol is utilized as the alcohol in either of the two preceding examples.

EXAMPLE VII

A series of oil formulations are prepared by combining with an SAE 30 motor oil 1% of the product of Examples I-VI. The products perform satisfactorily as dispersants and provide wear properties expected through boron incorporation.

EXAMPLE VIII

A gasoline based fuel is prepared utilizing 0.5% by weight of the boronated compound of Example III in gasoline. The product functions suitably as a fuel and provides boron anti-wear effects to the engine.

What is claimed is:

1. A process for boronating an amide, imide or Mannich base containing compound including the steps of mixing:
    (a) a compound containing an amide, imide or Mannich base group which has present at least one amine group or salt thereof;
    (b) a boronating agent, and;
    (c) a protic compound in a weight ratio to the boronating agent of at least about 1:2, and;
    (d) obtaining the boronated compound without removing the water of reaction as it is formed.
2. The process of claim 1 wherein the protic compound is a lower alcohol.
3. The process of claim 1 wherein the protic compound is water.
4. The process of claim 1 wherein the protic compound is a mixture of water and a lower alcohol.
5. The process of claim 2 wherein the lower alcohol contains up to about 10 carbon atoms.
6. The process of claim 4 wherein the weight ratio of the water to the alcohol is from about 10:1 to about 1:5.
7. The process of claim 3 wherein the water is present in at least a 3:5 weight ratio to the boronating agent.
8. The process of claim 1 wherein the molecular weight of component (a) is at least 250.
9. The process of claim 1 wherein the ratio of nitrogen equivalents in component (a) to the boron equivalents in component (b) is from about 4:1 to about 1:2.
10. The process of claim 4 wherein the product is substantially clear.
11. The process of claim 1 wherein the boron incorporated is from about 0.5% to about 5% by weight of the boronated compound.
12. The process of claim 2 wherein the alcohol is a monohydric alcohol.
13. The process of claim 12 wherein the alcohol is n-butanol.

14. The process of claim 1 wherein component (a) is a polyamine.

15. The process of claim 1 wherein the boronating agent is boric acid.

16. A boronated compound according to claim 1.

17. A process for boronating a compound containing an amine group including the steps of mixing:
   (a) a compound containing at least one amine group;
   (b) a boronating agent,
   (c) water, and
   (d) an alcohol wherein the combined weight of the water and the alcohol present is at least about 1 part per 2 parts of the boronating agent, and
   (e) obtaining the boronated compound.

18. A boronated compound according to claim 17.

19. The process of claim 17 wherein the amine is a polyamine.

* * * * *